United States Patent [19]
Hobo et al.

[11] Patent Number: 5,707,233
[45] Date of Patent: Jan. 13, 1998

[54] DENTAL ARTICULATOR

[75] Inventors: Sumiya Hobo, 5-3, Takanawa 4-chome, Minato-ku, Tokyo; Hisao Takayama, Tokyo, both of Japan

[73] Assignees: Shioda Dental Manufacturing Co., Ltd., Tochigi; Sumiya Hobo, Tokyo, both of Japan

[21] Appl. No.: 584,115

[22] Filed: Jan. 11, 1996

[30] Foreign Application Priority Data

Jun. 20, 1995 [JP] Japan .................. 7-153142

[51] Int. Cl.⁶ .................................. A61C 11/06
[52] U.S. Cl. ...................... 433/55; 433/56; 433/59
[58] Field of Search .................. 433/54, 55, 56, 433/57, 59, 61, 66

[56] References Cited

U.S. PATENT DOCUMENTS

| | | | |
|---|---|---|---|
| 2,389,101 | 11/1945 | Whittemore | 433/59 |
| 3,905,112 | 9/1975 | Swanson | 433/57 |
| 4,189,837 | 2/1980 | Stele | 433/57 |
| 4,305,708 | 12/1981 | Beu | 433/66 |
| 4,762,490 | 8/1988 | Ludwigs | 433/56 |
| 4,764,113 | 8/1988 | Hiranuma | 433/56 |

OTHER PUBLICATIONS

Sumiya Hobo, Herbert T. Shillingburg, Jr. and Lowell D. Whitseel, "Articulator Selection for Restorative Dentistry", J Prosthetic Dent., Vo., 36, No. 1, 1976, pp. 35–43.

Sara Jean Donegan and Larry V. Christensen, "Sagittal Condylar Guidance as Determined by Protrusion Records and Wear Facets fo Teeth", The International Journal of Prosthodontics, vol. 4, No. 5, 1991, pp. 469–472.

F.W. Craddock, "The Accuracy and Practical Value of Records of Condyle Path Inclination", The Journal of the American Dental Association, Vo. 38, No. 6, 1949, pp. 697–710.

Herbert T. Shillingburg, Jr., Sumiya Hobo and Lowell D. Whitsett, "Fundamentals of Fixed Prosthodontics", Second Edition, Quintessence Publishing Co., Inc., 1981, pp. 63–69, p. 270, pp. 278–282, pp. 289–291, pp. 294–297.

Albert Solnit and Donald C. Curnutte, "Occlusal Correction Principles and Practice", Quintessence Publishing Co., Inc., 1988, pp. 147–148.

*Primary Examiner*—Cary E. O'Connor
*Attorney, Agent, or Firm*—Watson Cole Stevens Davis, P.L.L.C.

[57] ABSTRACT

An articurator is comprised of a mandibular frame being provided with condyles, a maxillary frame mounted on the mandibular frame via condylar guide mechanisms, an anterior guide table provided on the front end of the mandibular frame, and an anterior guide pin provided on the front end of the maxillary frame. The anterior guide table comprises a table portion and lateral wings. The table portion has a sagittal inclination angle adjusting mechanism, and the lateral wings has lateral wing angles adjusting mechanisms. The anterior guide pin makes contact with and slides on an anterior guide mechanism formed by the surface of the anterior guide table. The condylar guide mechanisms in which the condyle is positioned have condylar path inclination angle adjusting mechanisms. The sagittal inclination angle, the lateral wing angles, and the condylar path inclination angles are to be adjusted by two steps to specified values of a first group and to specified values of a second group.

4 Claims, 5 Drawing Sheets

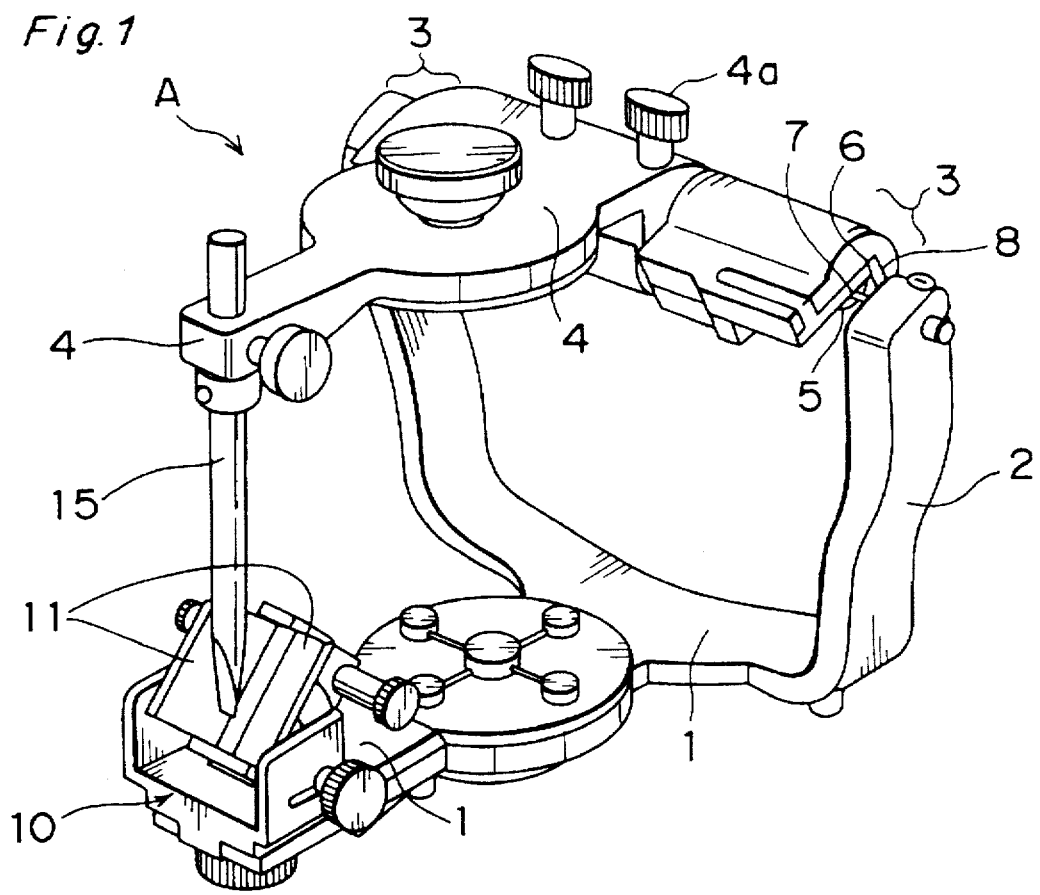
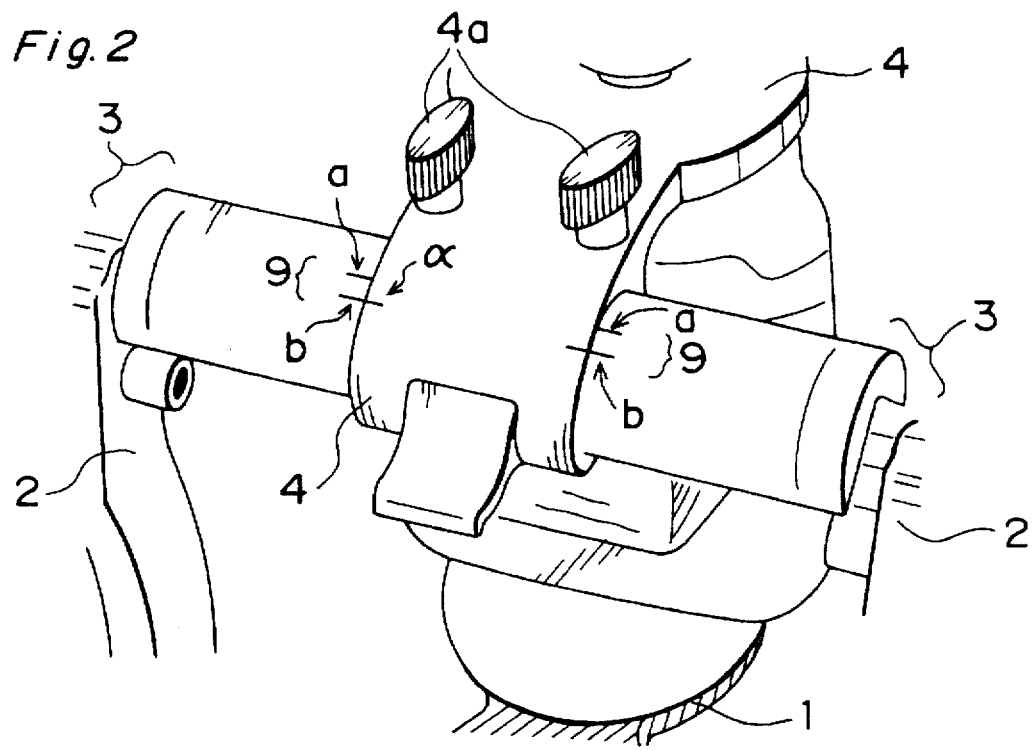

Fig. 5
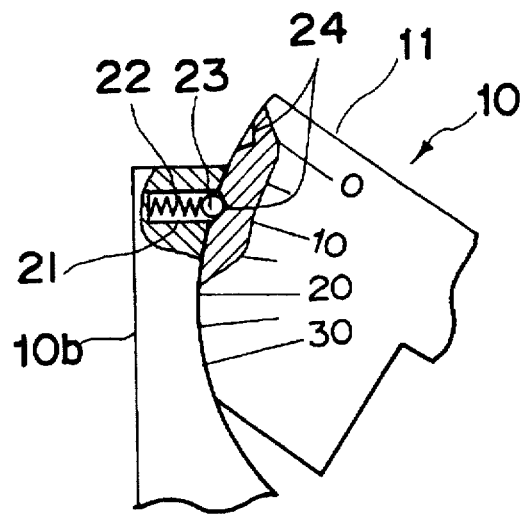
Fig. 6
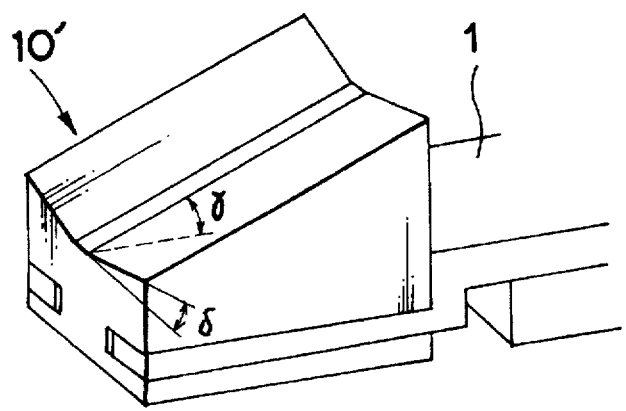
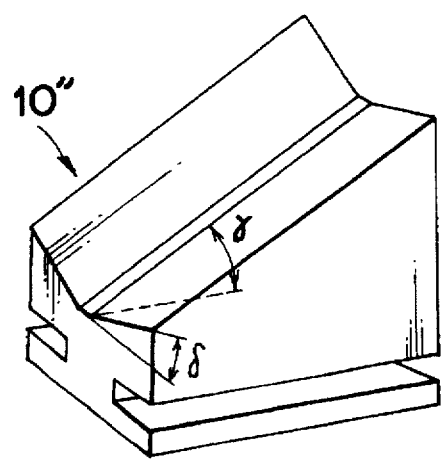

5,707,233

DENTAL ARTICULATOR

BACKGROUND OF THE INVENTION

1. Field of the Invention

The present invention relates to a dental articulator. More specifically this invention relates to a dental articulator in which a condylar guide mechanism and an anterior guide mechanism are provided with adjustable function.

2. Description of the Prior Art

As shown in FIG. 7, a dental articulator B generally comprises a mandibular frame 1 having arm portions 2 formed on left and right back ends thereof and a maxillary frame 4 mounted on upper ends of the arm portions 2 of the mandibular frame 1 via opening mechanisms 3. Each opening mechanism 3 (corresponding to a temporomandibular joint of a living body) is composed of a condyle 5 (corresponding to a condyle of the living body) provided on the upper end of the arm portion 2 of the mandibular frame 1 and a box-like portion 6 (corresponding to a glenoid fossa of the living body) formed in the maxillary frame 4 so as to surrounding the condyle 5. The maxillary frame 4 makes an opening movement around a rotational axis (intercondylar axis) defined by a line connecting centers of left and right condyles 5.

In the internal surface of the box-like portion 6 is formed an upper wall 7 as a condylar guide mechanism. The upper wall 7 inclines forwardly toward the lower direction at an angle α (sagittal condylar path inclination) with respect to a horizontal reference plane defined by the upper surface of the maxillary frame 4. The angle α is adjustable within a constant range by means of a hexagonal screw 4a. Moreover, in the internal surface of the box-like portion 6 is formed a rear wall 8 which obstructs the rear end of movement path of the condyle 5. When the articulator B makes an excursive movement, the condyle 5 is guided by the upper wall 7.

The sagittal condylar path inclination is set by the angle α. An adjusting scale 9 is notched on the upper surface of the maxillary frame 4 corresponding to the upper portion of the condylar guide mechanism at a pitch of 5 degrees within the range of generally 0–60 degrees so that the sagittal condylar path inclination α can be easily adjusted within a range.

Moreover, in the internal surface of the box-like portion 6 as shown in FIG. 8 is provided a lateral wall 8' as a second condylar guide mechanism. The lateral wall 8' inclines toward the internal direction at an angle β. The angle β is adjustable within a range or fixed to a specified value. By this angle β is set a Bennett angle during the lateral movement of articulator B. In the case of making the angle β adjustable within a constant range, the angle β is arranged so as to be adjustable within the range of generally 0–25 degrees.

On the other hand, at the front end of mandibular frame 1 is provided an anterior guide table 10 as an anterior guide mechanism, while at the front end of maxillary frame 4 is provided an anterior guide pin 15 which constitutes an vertical dimension holding mechanism between the maxillary frame 4 and the mandibular frame 1.

On the anterior guide table 10 is provided an sagittal inclination angle of γ with respect to the horizontal reference plane toward the base of the mandibular frame 1. Moreover, on the anterior guide table 10 are formed lateral wings 11 which incline at an angle δ with respect to the anterior guide table surface. The angles γ and δ are arranged so as to be specified values (shown in FIG. 7) or to be adjustable within a range. In the case of making the sagittal inclination of anterior guide table γ adjustable within a range, an adjusting scale 13 (shown in FIG. 9) is pitched on the side surface of a γ angle adjusting mechanism (not shown) provided under the bottom of the anterior guide table 10 at a pitch of 5 degrees within the range of generally 0–60 degrees. Further, in the case of making the lateral wing angle of anterior guide table δ adjustable within a range, an adjusting scales 14 (shown in FIG. 9) are pitched on the side surfaces of a δ angle adjusting mechanism (not shown) provided under the bottom of the anterior guide table 10 at a pitch of 5 degrees within the range of generally 0–45 degrees. $W_1$, $W_2$ are dentition casts mounted on the mandibular frame 1 and the maxillary frame 4 respectively by known means.

It has been common practice in dentistry so far that left and right sagittal condylar path inclinations α measured in an individual living body have to be reproduced on an articulator. So, the utilization of precise instruments such as pantograph and fully-adjustable articulator has been ideal for fabricating a restoration. However, the manipulations of the pantograph and fully-adjustable articulator require high skill, time and labor. In addition, the clinical effect corresponding to the labor has not been guaranteed. Therefore, under the present situation, the pantograph and fully-adjustable articulator have been hardly utilized at dental clinics or laboratories, whereas a semi-adjustable articulator has been used in some places, and in general a plane line articulator or a mean value articulator has been greatly used.

The plane line articulator makes only the movement around a rotational axis defined by an intercondylar axis and is possible to nearly simulate the opening movement of the mandible at empty jaw. Man by nature moves mandible to the right when chewing food with right molar teeth, and moves mandible to the left when chewing food with left molar teeth. In order to simulate such mandibular movement, it is necessary to move the front end of the maxillary frame of the articulator to the left or right side direction while bringing the mandibular teeth into contact with the maxillary teeth and sliding each other. Since the plane line articulator is not possible to make such movement, the correct occlusal relation between the mandibular teeth and the maxillary teeth is not obtained by means of the plane line articulator.

On the other hand, the mean value articulator has elements of the mandibular movement which are fixed to the anatomical mean values. Therefore, the mean value articulator is easy to manipulate and thereby broadly used. In human body, the separation between the cusps of the mandibular molar teeth and those of the maxillary molar teeth is made on the opposite side to the chewing side, that is, on the left side when chewing food with right molar teeth or on the right side when chewing food with left molar teeth. This phenomenon is called disocclusion, which is physiologically indispensable for protecting the molar teeth from horizontal occlusal pressure during the masticatory movement. The reverse phenomenon that the cusps of the mandibular and maxillary molar teeth interfere each other on opposite side to the chewing side is called a cuspal interference (a cross arch balance or a balancing contact) on nonworking side, which is one of the typical contraindications relating to the occlusal relation of the mandibular and maxillary teeth by reason that it is apt to induce symptoms such as occlusal wear, periodontitis, or temporomandibular disorders.

It is a generalized procedure in a daily clinical treatment to have a patient make a mandibular movement at the time of trying the restoration in the patient's mouth for performing the occlusal adjustment and to grind a region which is recognized to be a cuspal interference. It is also a common practice to stop the grinding work at the time when the cuspal interference is removed. Then, the amount of disocclusion of the ground region must be approximately zero. According to this procedure, therefore, the proper amount of disocclusion is not obtained. In the case of fabricating the restoration by utilizing the mean value articulator, it is not possible in the same way as the aforementioned clinical treatment to obtain a proper amount of disocclusion to the restoration.

In the anterior guide mechanism of prior art, the standards for adjusting the sagittal inclination angle γ and lateral wing angles δ of the anterior guide table 10 have not been established. Therefore, the anterior guide table 10 with the adjusting mechanisms as shown in FIG. 9 has not been practically used, while in general the anterior guide table with the angles γ and δ fixed to respectively one specified value as shown in FIG. 7 or a flat board type anterior guide table (not shown) have been greatly used. It is a common sense in dentistry that the mandibular movement is represented by the movement of mandibular triangle formed by the left and right condyles and the incisal point. The fact that there has been no criteria for adjusting the anterior guide mechanism is equivalent to the fact that the front one apex among the three apices of the mandibular triangle is disregarded. It is also well known that anterior guidance is one of the important factor influencing disocclusion. Therefore, if the mandibular guidance is disregarded, the proper amount of disocclusion will not be obtained and the satisfactory restoration can not be fabricated.

Thus, according to the prior art, it is very difficult to perform the occlusal adjustment so that the proper amount of disocclusion is obtained not only in the oral cavity but also on the articulator. If the dental clinic treatment is left as such situation, the patient satisfaction will be temporary obtained, but it will be possible that the latent causes for such as occlusal wear, periodontitis, or temporomandibular disorders are neglected. This is extremely undesirable situation.

Therefore, at the time of fabricating the restoration as well as the occlusal adjustment in the patient's oral cavity, in advance, the proper amount of disocclusion has to be realized on the dentition casts mounted on the articulator and then transferred to the oral cavity.

SUMMARY OF THE INVENTION

According to the recent scientific and systematic research with respect to the occlusion, a procedure for providing a proper amount of disocclusion to the dentition cast mounted on the articulator has been established by the inventors of the present invention. This procedure has been obtained as a result of computed analyses utilizing many measurement data in combination with the theory of mandibular movement. The gist of main conclusion of the research and method of the procedure will be explained hereinafter.

1) Conclusion (1) The criteria for the occlusal restoration has been the measurement value of condylar path, by which the adjustment of articulator has been conducted. However, it has been clarified by the inventors that the condylar path is not possible to be criteria for the occlusal restoration, because the measurement value of condylar path in a living body deviate largely. So, there is no clinical significance in measuring the condylar path in each patient by the pantograph or the like.

(2) The semi-adjustable articulator is enough as a articulator, while the fully adjustable articulator is not necessary at all.

(3) The incisal path is not possible to be criteria for the occlusal restoration either, because the measurement value of incisal path vary largely between individual living bodies.

(4) As a result of research mentioned before, it has been understood that the amount of disocclusion has three factors, that is, condylar path, incisal path and cusp slope angle. In addition, it has become clear that the factor having the highest reliability as criteria of occlusion is cusp slope angle. Therefore, standard values of cusp slope angles should be used as the criteria of occlusion so that the proper amount of disocclusion can be obtained.

(5) The standard values of cusp slope angle with respect to the specified horizontal reference plane are 25 degrees along the protrusive path of opposing cusp, 20 degrees along the lateral path on nonworking side, 15 degrees along the lateral path on working side.

(6) In order to fabricate the cuspal morphology of a restoration having the abovementioned standard values of cusp slope angle on the articulator, a condition that the cusps of the mandibular and maxillary molars come into contact with and slide each other while making the excursive movement of the articulator has to be produced. However, this condition is interrupted by the anterior teeth. Because the presence of anterior teeth causes the mandibular and maxillary molars to separate according to the anterior guidance, which eliminates the mandibular and maxillary molars from coming into contact with and slide each other. Therefore, in order to fabricate the cuspal morphology of a restoration, it is necessary to make the anterior teeth portion of the dentition casts detachable. Then, as a first step the anterior teeth portion should be detached from the dentition casts to set a condition by utilizing the anterior guide table of the articulator so that the cusps of the mandibular and maxillary molars come into contact with and slide each other. In this case, the adjustment value of the condylar path inclination is to be set to the lower limit of the statistical deviation in a living body. The adjustment condition of articulator used in the first step is called "Condition 1".

(7) After the standard value of cusp slope angle is provided at the first step, the anterior teeth portion is returned to the dentition casts. If the normal anterior guidance is provided, then the dentition casts expressing the normal amount of disocclusion will be obtained. In this case, the adjustment value of the condylar path inclination is to be set to a standard value in a living body. Under this condition, the anterior guide table of the articulator is set so that the standard value of the incisal path can be obtained, then the restoration of palatal surface of maxillary anterior teeth is performed. The adjustment condition of articulator used in this second step is called "Condition 2".

2) Method (1) Upon fabricating a restoration or conducting an occlusal diagnosis and adjustment on dentition casts mounted on an articulator, the anterior teeth portion is made detachable from the dentition casts by a known method using Dowel pins. Then, two steps are conducted. In the first step, the cuspal morphology of dentition is restorated or adjusted under the condition that the anterior teeth is detached from the dentition cast. In the second step, the anterior teeth is returned to the dentition casts and restorated or adjusted. Thereby, an ideal occlusal condition in which the proper and uniform amount of disocclusion is occured over the whole molar dentition is realized. In this connection, the standard values of the amount of disocclusion are 1.0 mm at a condylar displacement of 3 mm during protrusive movement, 1.0 mm on nonworking side and 0.5 mm on working side at a condylar displacement of 3 mm during lateral movement.

(2) Table 1 shows criteria for adjustment values in the Condition 1 which is the adjustment condition of articulator in the first step and in the Condition 2 which is the adjustment condition of articulator in the second step, which were calculated by a compitcheder based on the measured data of the amount of disocclusion and the mathematical model of mandibular movement.

TABLE 1

CRITERIA FOR ADJUSTMENT VALUES OF ARTICULATOR
(unit: degree)

|  | Condylar path | | Anterior guide table | |
| --- | --- | --- | --- | --- |
|  | Inclination angle ($\alpha$) | Bennett angle ($\beta$) | Inclination angle ($\gamma$) | Lateral wing angle ($\delta$) |
| Condition 1 | 25 | 15 | 25 | 10 |
| Condition 2 | 40 | 15 | 45 | 20 |

Since the adjustment value of Bennett angle ($\beta$) in the condition 1 is set to the same value as that in the condition 2 as shown in Table 1, the Bennett angle needs not to be adjusted between the condition 1 and 2 but can be a fixed value.

The present invention has been developed with a view to applying the new clinical procedure for fabricating a restoration summarized above in 2) to actual clinical work.

According to the experience of clinical treatment on both articulator and living body, the following effects have been verified. Applying the adjustment values of articulator in Conditions 1 and 2 as shown in Table 1 to the new clinical procedure of restoration enables the fabrication of good quality restoration which expresses the proper and uniform amount of disocclusion, and also steeply raises the degree of accuracy of occlusal diagnosis or adjustment.

The new clinical procedure is possible to be practiced on the dental articulator of prior art which is provided with the adjusting scale of condylar path inclination angle as shown in FIG. 7 and the adjusting scale of anterior guide table as shown in FIG. 9 and which covers the adjustment values described in Table 1 in the ranges of the adjusting scales. However, in order to certainly have the effects of the new clinical procedure, the adjusting scales of the articulator have to be correctly adjusted to the values in Conditions 1 and 2 as shown in Table 1 every time. It is easy to say but almost impossible to do that the adjustment values are confirmed at every time of adjustment work in the busy clinic or laboratory to expect no mistake. As the technician becomes used to conducting the adjustment, he is apt to trust his memory in the adjustment values, and then believes the incorrect value to be correct and repeats the same mistake many times. This has been a trying experience actually happened under the clinical treatment according to the present procedure.

Since the one adjustment work of Condition 1 or 2 as shown in Table 1 needs total five adjustments of the left and right condylar path inclination angles, the anterior guide table inclination angle, and the left and right lateral wing angles of anterior guide table, it takes around 1 minutes to conduct one adjustment work. In the case of fabricating large scale restoration, when conducting such adjustment work carefully, it is repeated dozens of times. Thus, the time of adjustment work can not be disregarded on the efficiency of the work.

Therefore, no matter how remarkable the effect of the new clinical procedure is, it is an essential requirement for spreading the present procedure, improving the quality of restoration and improving the degree of accuracy of occlusal diagnosis or adjustment to simplify the adjustment work within the range of possibility.

The object of the present invention is therefore to provide a dental articulator which has necessary and sufficient functions to satisfy the adjustment conditions of Condition 1 and 2 as shown in Table 1 and in which the adjustment work is remarkably simplified as compared to the prior art.

In a first aspect of the invention, there is provided a dental articulator, comprising:

a mandibular frame having arms at left and right rear ends, on upper ends of said arms being provided with condyles;

an maxillary frame mounted on upper ends of the arms of the mandibular frame via opening mechanisms;

an anterior guide table provided on the front end of the mandibular frame, the anterior guide table comprising a table portion and lateral wings provided on both sides of the table portion, the table portion having a sagittal inclination angle adjusting mechanism, the lateral wings having lateral wing angles adjusting mechanisms;

an anterior guide pin provided on the front end of the maxillary frame, the anterior guide pin making contact with and sliding on an anterior guide mechanism formed by the surface of the anterior guide table;

condylar guide mechanisms which comprises upper and rear walls formed on the maxillary frame and an inner lateral wall of a Bennett angle providing element provided on the maxillary frame, and in which the condyle is positioned, whereby the condyle being possible to relatively move downward toward the front direction with respect to the maxillary frame, the condylar guide mechanisms having condylar path inclination angle adjusting mechanisms which adjust the inclination of condylar path; and whereby the sagittal inclination angle and the lateral wing angles of the anterior guide table, and the condylar path inclination angles are to be adjusted by two steps to specified values of a first group and to specified values of a second group.

Preferably, at least any one of the sagittal inclination angle adjusting mechanisms and the lateral wing angles adjusting mechanisms of the anterior guide table, and the condylar path inclination angle adjusting mechanisms may have adjusting scales, the scales being marked so that the specified values of the first group and the second group are possible to distinguish from other general values.

Preferably, at least any one of the sagittal inclination angle adjusting mechanisms and the lateral wing angles adjusting mechanisms of the anterior guide table, and the condylar path inclination angle adjusting mechanisms may have stopper mechanisms by which each adjusting range is limited to the specified values of the first group and the second group.

Preferably, the Bennett angle may be 15 degrees, and wherein the specified values of the first group for the sagittal inclination angle $\gamma$ and the lateral wing angles $\delta$ of the anterior guide table, and the sagittal condylar path inclination $\alpha$ are respectively 25 degrees, 10 degrees, and 25 degrees, while the specified values of the second group for the sagittal inclination angle $\gamma$ and the lateral wing angles $\delta$ of the anterior guide table, and the sagittal condylar path inclination $\alpha$ are respectively 45 degrees, 20 degrees, and 40 degrees.

In a second aspect of the invention, there is provided a dental articulator, comprising:

a mandibular frame having arms at left and right rear ends, on upper ends of said arms being provided with condyles;

an maxillary frame mounted on upper ends of the arms of the mandibular frame via opening mechanisms;

an anterior guide table provided on the front end of the mandibular frame, the anterior guide table comprising a table portion with upper surface inclined downward toward the front direction and lateral wings provided on both sides of the table portion;

an anterior guide pin provided on the front end of the maxillary frame, the anterior guide pin making contact with and sliding on an anterior guide mechanism formed by the surface of the anterior guide table;

condylar guide mechanisms which comprises upper and rear walls formed on the maxillary frame and an inner lateral wall of a Bennett angle providing element provided on the maxillary frame, and in which the condyle is positioned, whereby the condyle being possible to relatively move downward toward the front direction with respect to the maxillary frame, the condylar guide mechanisms having condylar path inclination angle adjusting mechanisms which adjust the sagittal condylar path inclination; and whereby the anterior guide table comprises two anterior guide tables which are replaceable with each other, one of the anterior guide tables having the sagittal inclination angle and the lateral wing angles fixed to specified values of a first group, the other of the anterior guide tables having the sagittal inclination angle and the lateral wing angles fixed to specified values of a second group.

An articulator having replaceable anterior guide tables is also provided in the prior art. However, such anterior guide tables are only the combination of flat type and angle fixed type, or the combination of anterior guide tables having the sagittal inclination angle and lateral wing angles of same fixed values of 0 degree, 5 degrees, 10 degrees, and 15 degrees respectively which are replaceable in accordance with the cases, because any criteria for adjusting the sagittal inclination angle and the lateral wing angles of the anterior guide table have not been established in prior art as described above.

Preferably, the specified values of the first group for the sagittal inclination angle γ and the lateral wing angles δ of the anterior guide table may be respectively 25 degrees, 10 degrees, while the specified values of the second group for the inclination angle γ and the lateral wing angles δ of the anterior guide table are respectively 45 degrees, 20 degrees.

According to the present inventions, the two-steps changeover work of adjustment values which is indispensable to the new clinical procedure is simply and easily performed. Although it has been taken about 60 seconds to perform the changeover manipulation by a conventional articulation, it takes about 30 seconds by the articulator having the colored adjustable scale, about 20 seconds by the articulator having the adjustable scale with the stopper mechanism, about 10 seconds by the articulator having the replaceable anterior guide table, this means that the changeover work is performed in time saving manner. Moreover, in any type of articulator, it is not necessary for the manipulator to confirm the specified adjustment values in Table 1 one by one, which reduces manipulator's stress during the manipulation and reduces the provability of miss-adjustment to approximately one to hundred.

BRIEF DESCRIPTION OF THE DRAWINGS

These and other objects and features of the present invention will become clear from the following description taken in conjunction with the preferred embodiments thereof with reference to the accompanying drawings, in which:

FIG. 1 is a perspective view of a dental articulator according to the present invention;

FIG. 2 is a partial perspective rear view of the dental articulator of FIG. 1;

FIG. 5 is a partially broken front view of the anterior guide table with a stopper mechanism;

FIG. 6 is perspective views of the two fixed type anterior guide tables replaceable with each other;

DETAILED DESCRIPTION OF THE PREFERRED EMBODIMENTS

Figure 7:
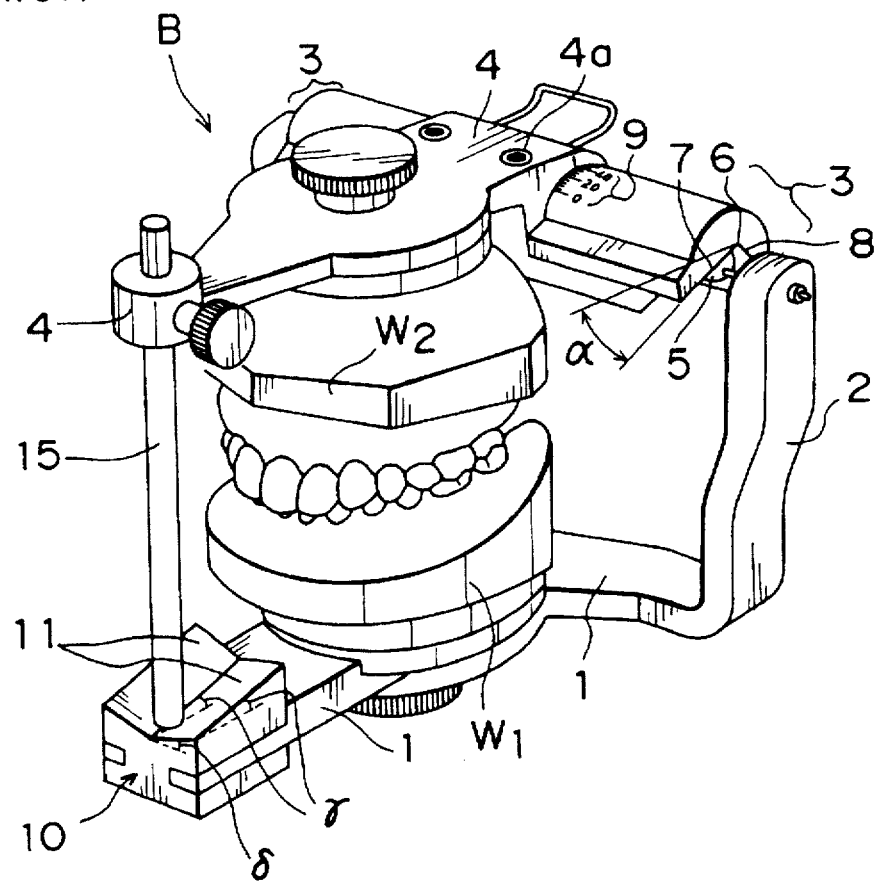
FIG. 7 is a perspective view of a dental articulator of prior art.
Figure 8:
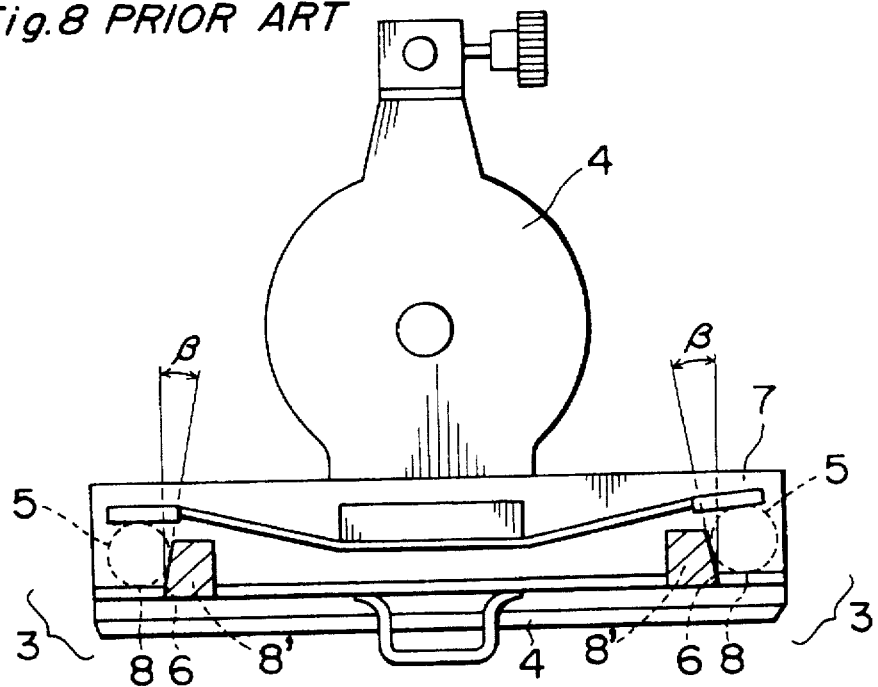
FIG. 8 is a bottom view of a maxillary frame of the dental articulator of FIG. 7.
Figure 9:
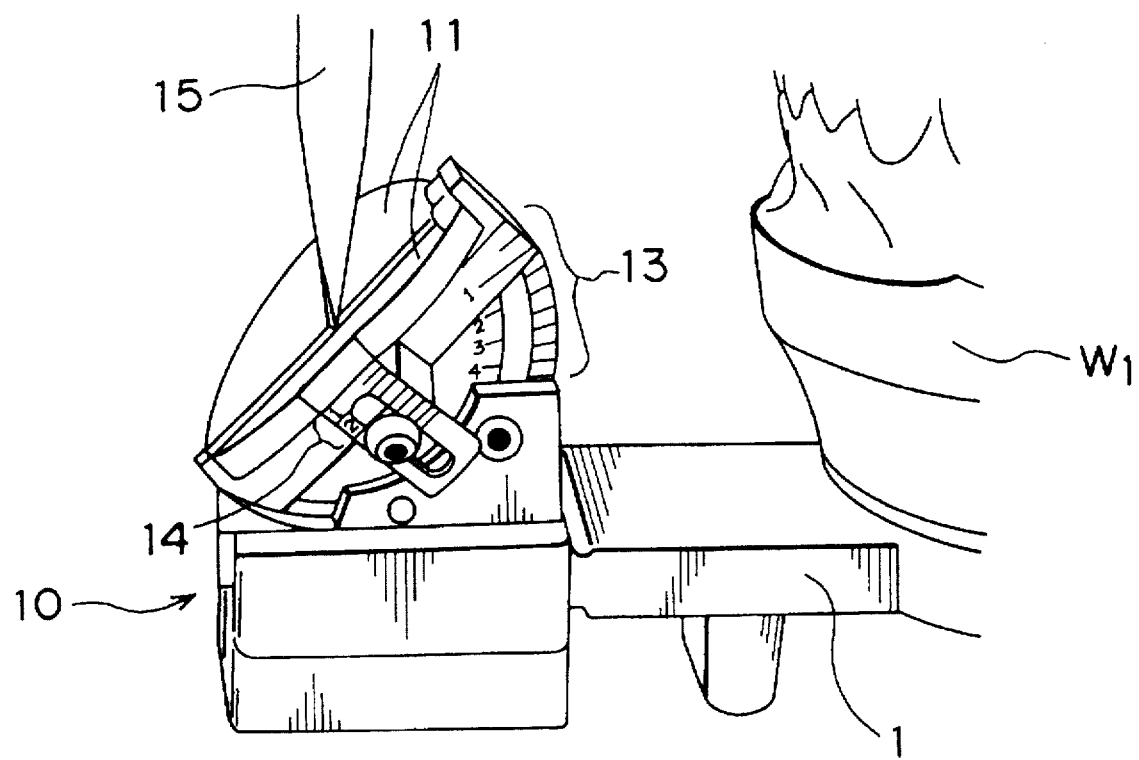
FIG. 9 is a partial perspective view showing an anterior guide table of an another dental articulator of prior art.

In FIGS. 1–4, same parts as that in FIGS. 7, 8 and 9 are designated by same numerals to omit description thereof.

Comparing FIGS. 1–4 with FIGS. 7, 8 and 9, it will be clear that two kinds of pitches, i.e., (a) and (b) for the adjusting scale 9 of sagittal condylar path inclination α are pitched on the maxillary frame 4. The pitch (a) is to be a red line and indicates 25 degrees (Condition 1 as shown in Table 1), while the pitch (b) is a blue line and indicates 40 degrees (Condition 2 as shown in Table 1). The Bennett angle β is fixed to 15 degrees.

The anterior guide table 10 provided on the front end of the mandibular frame 1 has substantially same construction as that of FIG. 9. The sagittal inclination angle γ of a table portion 10b is to be adjustable by a adjusting knob 16 and read out from a scale 13 with an upper edge of body frame 10a. The scale 13 is pitched within the range of 0–60 degrees. The 25 degrees (Condition 1 as shown in Table 1) and the 45 degrees (Condition 2 as shown in Table 1) are distinguished from other degrees by a red line and characters (a) and a blue line and characters (b).

The lateral wing angles δ of lateral wings 11, 11 are to be adjustable by adjusting knobs 17, 17 and read out from scales 14 with a reference line pitched on the table portion 10b. The each scale 14 is pitched within the range of 0–40 degrees. The 10 degrees (Condition 1 as shown in Table 1) and the 20 degrees (Condition 2 as shown in Table 1) are distinguished from other degrees by a red line and characters (a) and a blue line and characters (b).

In the case of conducting an occlusal adjustment of dentition casts $W_1$, $W_2$ mounted on the frames by the aforementioned articulator A, the dentition casts $W_1$, $W_2$ in which the anterior portion is removable by using Dowel pins are used. The anterior portion is removed from the dentition casts. Then, the dentition casts are mounted on the maxillary frame 4 and the mandibular frame 1. The sagittal condylar path inclination α, the sagittal inclination angle γ and the lateral wing angles δ of anterior guide table are adjusted to respectively 25 degrees, 25 degrees, and 10 degrees. By manipulating the articulator A, cusps of upper and lower molars are made contact with each other to slide. Then restoration work is performed so that the cusp slope angles of molars become uniform. In this case, the dentition casts have no anterior dentition, which does not cause anterior guidance. Therefore, the restoration work of posterior dentition is easily and precisely performed by sliding the tip of the anterior guide pin 15 on the surface of the anterior guide table 10.

Then, the anterior portion is returned to the dentition casts. The sagittal condylar path inclination α, the sagittal inclination angle γ and the lateral wing angles δ of anterior guide table are adjusted to respectively 40 degrees, 45 degrees, and 20 degrees. After that, the restoration work of anterior dentition is easily and precisely performed by sliding the tip of the anterior guide pin 15 on the surface of the anterior guide table 10.

In aforementioned embodiment, the specified values of the first and second groups are manually adjusted by the adjusting knobs 16, 17, 17 and by using red and blue lines as a landmark. In another embodiment as shown in FIG. 5, however, such values may be adjusted by stopper mechanisms, which makes changeover operations more easier.

The each stopper mechanism is comprised of a ball 23 and two depressed portions 24. The ball 23 is housed in a hole 21 formed on the table portion 10b and is supported by a spring 22 so that the ball 23 protrudes toward the outside of the hole 21. The depressed portions 24 are formed on the side surface of the lateral wing 11 so as to receive the ball 23. When the one of the depressed portions 24 receives the ball 23, the lateral wing angle δ is set to 10 degrees of Condition 1. And, when the other of the depressed portions 24 receives the ball 23, the lateral wing angle δ is set to 20 degrees of Condition 2.

Moreover, in aforementioned embodiment, the adjusting scale 9 of sagittal condylar path inclination α has only two pitches indicating the specified values of the first and second groups as shown in FIG. 2. In another embodiment, however, the adjusting scale 9 may have pitches within the ranges of 0-60 degrees, whereby the articulator is possible to be used as a semi-adjustable articulator.

Figure 3:
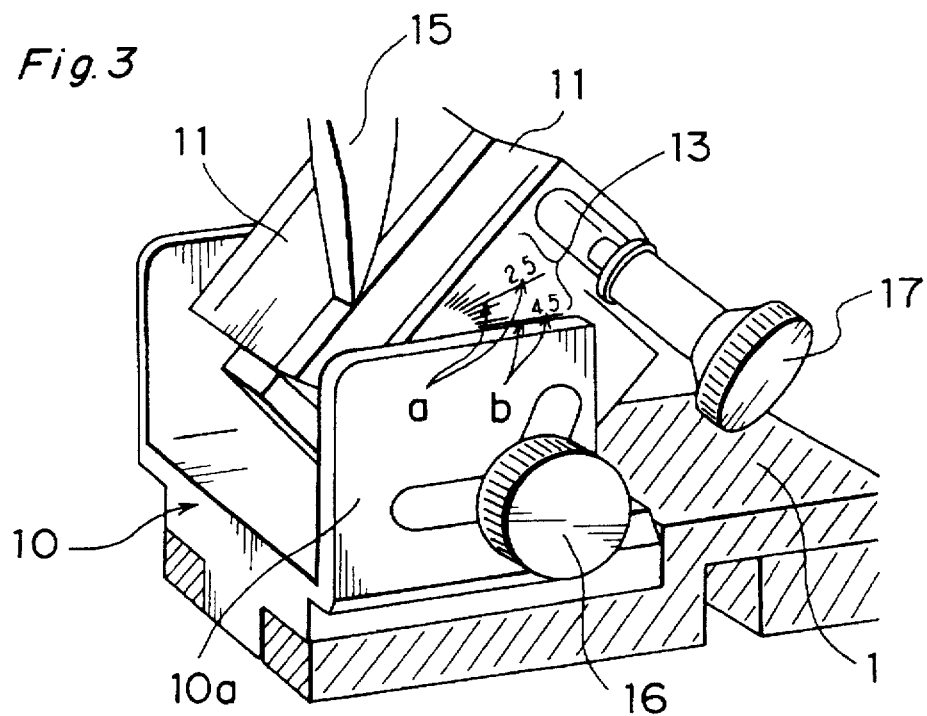
FIG. 3 is a partial perspective view of an anterior guide table of the dental articulator of FIG. 1.
Figure 4:
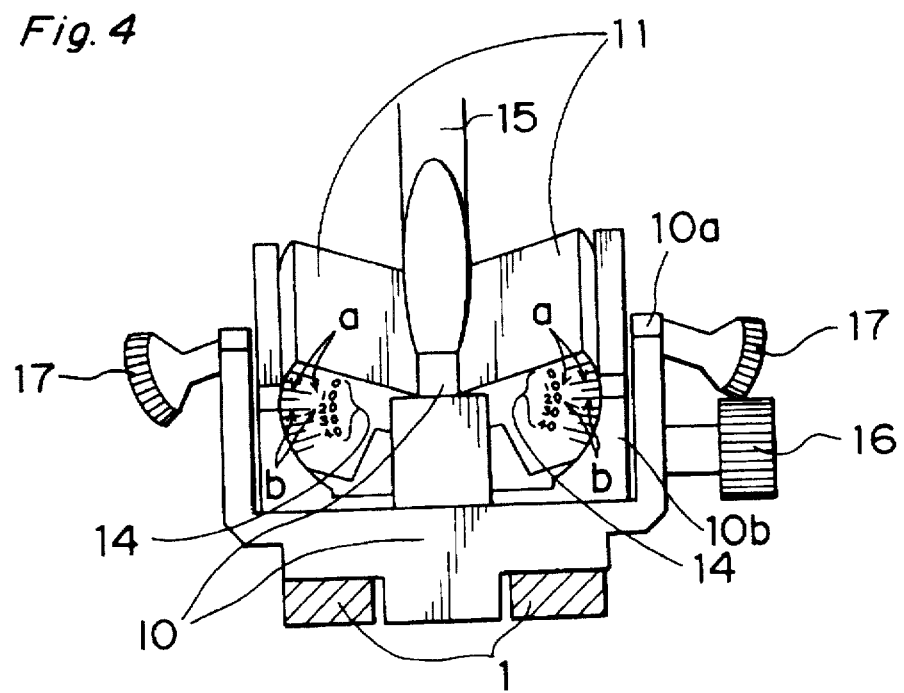
FIG. 4 is a front view of the anterior guide table of FIG. 3.

Moreover, in aforementioned embodiment, the anterior guide table 10 is possible to adjust both the sagittal inclination angle γ and the lateral wing angles δ as shown in FIGS. 3 and 4. In another embodiment, however, two angle-fixed type anterior guide tables 10', 10" as shown in FIG. 6 having both the sagittal inclination angle γ and the lateral wing angles δ fixed to the specified values of the first and second groups may be replaceable mounted on the front end of the mandibular frame 1.

The specified values as shown in Table 1 are to be used at the present time. However, it will be modified in future to the extent of ±5 degrees due to the change in the framework of human body.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A dental articulator, comprising:

a mandibular frame having arms at the left and right rear ends, upper ends of said arms being provided with condyles;

a maxillary frame mounted on the upper ends of the arms of the mandibular frame via opening mechanisms;

an anterior guide table provided on a from end of the mandibular frame, the anterior guide table comprising a table portion and lateral wings provided on both sides of the table portion, the table portion having a sagittal inclination angle adjusting mechanism, the lateral wings having lateral wing angles adjusting mechanisms;

an anterior guide pin provided on the front end of the maxillary frame, the anterior guide pin making contact with an sliding on an anterior guide mechanism formed by the surface of the anterior guide table;

condylar guide mechanisms which comprises upper and rear walls formed on the maxillary frame and an inner lateral wall of a Bennett angle providing element provided on the maxillary frame, and in which the condyle is positioned, whereby the condyle being possible to relatively move downward toward the front direction with respect to the maxillary frame, the condylar guide mechanisms having condylar path inclination angle adjusting mechanisms which adjust the sagittal inclination of condylar path; and whereby the sagittal inclination angle and the lateral wing angles of the anterior guide table, and the condylar path inclination angles are to be adjusted by two steps to specified values of a first group and to specified values of a second group, and wherein at least one of the sagittal inclination angle adjusting mechanisms and the lateral wing angles adjusting mechanisms of the anterior guide table and the condylar path inclination angle adjusting mechanisms have adjusting scales, the scales being marked so that the specified values of the first group and the second group are possible to distinguish from other general values.

2. A dental articulator as set forth in claim 1, wherein at least any one of the sagittal inclination angle adjusting mechanisms and the lateral wing angles adjusting mechanisms of the anterior guide table, and the condylar path inclination angle adjusting mechanisms have stopper mechanisms by which each adjusting range is limited to the specified values of the first group and the second group.

3. A dental articulator as set forth in claim 2, wherein the Bennett angle is 15 degrees, and wherein the specified values of the first group for the sagittal inclination angle γ and the lateral wing angles δ of the anterior guide table, and the sagittal inclination of condylar path α are respectively 25 degrees, 10 degrees, and 25 degrees, while the specified values of the second group for the sagittal inclination angle γ and the lateral wing angles δ of the anterior guide table and the inclination of condylar path α are respectively 45 degrees, 20 degrees, and 40 degrees.

4. A dental articulator as set forth in claim 1, wherein the Bennett angle is 15 degrees, and wherein the specified values of the first group for the sagittal inclination angle γ and the lateral wing angles δ of the anterior guide table, and the sagittal inclination of condylar path α are respectively 25 degrees, 10 degrees, and 25 degrees, while the specified values of the second group for the sagittal inclination angle γ and the lateral wing angles δ of the anterior guide table and the inclination of condylar path α are respectively 45 degrees, 20 degrees, and 40 degrees.

* * * * *